(12) United States Patent
Lemieux et al.

(10) Patent No.: US 8,439,630 B2
(45) Date of Patent: May 14, 2013

(54) OPTICAL MONITORING SYSTEM FOR A TURBINE ENGINE

(75) Inventors: Dennis H. Lemieux, Casselberry, FL (US); Jan P. Smed, Winter Springs, FL (US); James P. Williams, Orlando, FL (US); Vinay Jonnalagadda, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 561 days.

(21) Appl. No.: 12/727,582

(22) Filed: Mar. 19, 2010

(65) Prior Publication Data

US 2011/0229307 A1 Sep. 22, 2011

(51) Int. Cl.
*G02B 23/00* (2006.01)
*F01D 25/00* (2006.01)

(52) U.S. Cl.
USPC ........... 415/118; 356/43; 374/144; 356/241.1

(58) Field of Classification Search ..... 415/118; 356/43, 356/241.1; 350/63; 60/39.75; 374/144; 73/116
See application file for complete search history.

(56) References Cited

U.S. PATENT DOCUMENTS

| | | | | |
|---|---|---|---|---|
| 4,306,835 A | * | 12/1981 | Hurley | 415/118 |
| 4,738,528 A | * | 4/1988 | Craft | 356/43 |
| 4,836,689 A | * | 6/1989 | O'Brien et al. | 374/125 |
| 5,146,244 A | * | 9/1992 | Myhre et al. | 359/509 |
| 5,185,996 A | | 2/1993 | Smith et al. | |
| 7,231,817 B2 | | 6/2007 | Smed et al. | |

FOREIGN PATENT DOCUMENTS

| | | | |
|---|---|---|---|
| GB | 2121978 A | * | 1/1984 |
| GB | 2127174 A | | 1/1984 |
| GB | 2127174 A | * | 4/1984 |
| WO | 8902069 A1 | | 3/1989 |
| WO | 9111694 A1 | | 8/1991 |

\* cited by examiner

*Primary Examiner* — Nathaniel Wiehe
*Assistant Examiner* — Joshua R Beebe

(57) ABSTRACT

The monitoring system for a gas turbine engine including a viewing tube assembly having an inner end and an outer end. The inner end is located adjacent to a hot gas flow path within the gas turbine engine and the outer end is located adjacent to an outer casing of the gas turbine engine. An aperture wall is located at the inner end of the viewing tube assembly and an optical element is located within the viewing tube assembly adjacent to the inner end and is spaced from the aperture wall to define a cooling and purge chamber therebetween. An aperture is defined in the aperture wall for passage of light from the hot gas flow path to the optical element. Swirl passages are defined in the viewing tube assembly between the aperture wall and the optical element for passage of cooling air from a location outside the viewing tube assembly into the chamber, wherein swirl passages effect a swirling movement of air in a circumferential direction within the chamber.

17 Claims, 3 Drawing Sheets

OPTICAL MONITORING SYSTEM FOR A TURBINE ENGINE

This invention was made with U.S. Government support under Contract Number DE-FC26-01NT41232 awarded by the U.S. Department of Energy. The U.S. Government has certain rights to this invention.

FIELD OF THE INVENTION

This invention is directed generally to turbine engines and, more particularly, to monitoring systems for monitoring components in a hot gas path of a gas turbine engine.

BACKGROUND OF THE INVENTION

Inaccessible or confined areas such as, for example, the interior parts of gas turbine engines, often require routine inspection to verify the integrity of internal engine parts and maintain safe operation of the engine by identifying potential problems, i.e., defects in a part, prior to failure of the part, or to identify the source of an existing problem. For example, problems may be identified through visual inspection by use of a borescope, such as during routine downtime maintenance of the gas turbine engine.

Additional optical monitoring of the turbine engine may be performed during operation of the engine to further identify the condition of components located within the hot gas path of the engine. Optical monitoring of engine components during operation of the engine requires that optical elements be placed inside the engine, potentially exposing them to temperatures that are higher than the operable range of the optical materials. In a known system, external cooling has been added to the system in the form of compressed cool air, water or liquid nitrogen to cool the optical elements below the maximum operable temperature. This solution has typically added substantial complexity and additional cost to the optical system. Further, since the optical elements must be cooled continuously during operation of the engine, it is preferable to utilize such externally cooled systems on only a short term basis.

SUMMARY OF THE INVENTION

In accordance with one aspect of the invention, a monitoring system for a gas turbine engine is provided. The monitoring system comprises a viewing tube assembly having an inner end and an outer end. The inner end is located adjacent to a hot gas flow path within the gas turbine engine and the outer end is located adjacent to an outer casing of the gas turbine engine. An aperture wall is located at the inner end of the viewing tube assembly, the aperture wall extending radially inwardly from an interior surface of the viewing tube assembly. An optical element is located within the viewing tube assembly adjacent to the inner end and is spaced from the aperture wall to define a cooling and purge chamber therebetween. An aperture is defined in the aperture wall for passage of light from the hot gas flow path to the optical element. One or more swirl passages are defined in the viewing tube assembly between the aperture wall and the optical element for passage of cooling air from a location outside the viewing tube assembly into the chamber, wherein the one or more swirl passages effect a swirling movement of air in a circumferential direction within the chamber.

In accordance with another aspect of the invention, a monitoring system is provided for a gas turbine engine comprising a radially outer casing wall and a radially inner casing surrounding a hot gas path through the turbine engine. The monitoring system comprises a viewing tube assembly having an inner end and an outer end. The inner end is located adjacent to the inner casing wall and the outer end is located adjacent to the outer casing wall of the gas turbine engine. An aperture wall is located at the inner end of the viewing tube assembly, the aperture wall extending radially inwardly from an interior surface of the viewing tube assembly. An optical element is located within the viewing tube assembly adjacent to the inner end and is spaced from the aperture wall to define a cooling and purge chamber therebetween. An aperture is defined in the aperture wall for passage of light from the hot gas flow path to the optical element. A plurality of circumferentially spaced swirl passages extend from an exterior surface to the interior surface of the viewing tube assembly and are located adjacent to the optical element for passage of cooling air from a location outside the viewing tube assembly into the chamber, wherein the swirl passages are each angled relative to an inward direction passing through a central longitudinal axis of the viewing tube assembly to effect a swirling movement of air in a circumferential direction within the chamber and subsequent flow of the cooling air out of the chamber through the aperture.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
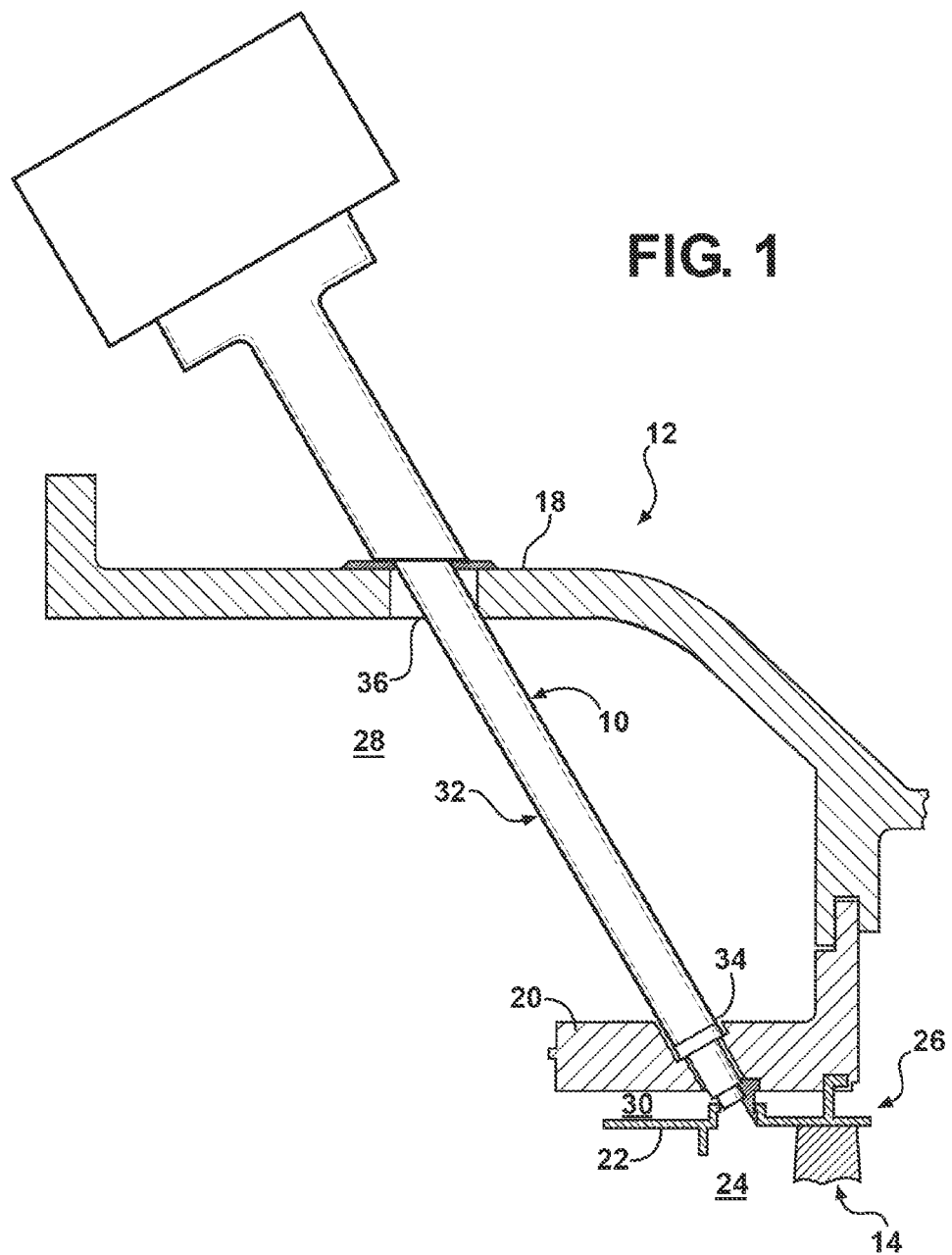
FIG. 1 is a cross-sectional view through a portion of a turbine engine and depicting a monitoring system in accordance with the present invention.

Referring to FIG. 1, a monitoring system 10 is illustrated for providing imaging of a component in a gas turbine engine 12 during operation of the turbine engine 12. In particular, the imaging system 10 is shown mounted to the turbine engine 12 and positioned extending between a radially outer casing wall 18 and in an inner casing wall 20 located radially inwardly from the outer casing wall 18 in a turbine section 26 of the turbine engine 12. The radially inner casing wall 20 supports an annular blade ring or shroud structure 22. The inner casing wall 20 and annular shroud structure 22 surround a hot gas path 24 extending through the turbine section 26 of the turbine engine 12.

An area between the outer casing wall 18 and the inner casing wall 20 comprises a shell area 28 for containing shell air comprising air provided from an exit of a compressor section (not shown) to a combustor section (not shown) of the turbine engine 12. In addition, a vane cooling air passage 30 is defined between the inner casing wall 20 and the annular shroud structure 22 for providing cooling air to rows of stationary vanes (not shown) in a conventional manner, such as by providing bleed air from one or more stages of the compressor section. In the illustrated embodiment, the monitoring system 10 may be provided for imaging a location on a component comprising an elongated turbine blade 14.

The monitoring system 10 comprises a viewing tube assembly 32 having an inner end 34 located adjacent to the inner casing wall 20 and an outer end 36 located adjacent to the outer casing wall 18 of the gas turbine engine 12. The viewing tube assembly 32 may comprise an assembly of one or more tubular elements. For example, the viewing tube assembly 32 may generally comprise a structure substantially similar to that described in U.S. Pat. No. 7,231,817, which patent is incorporated herein by reference.

Figure 2:
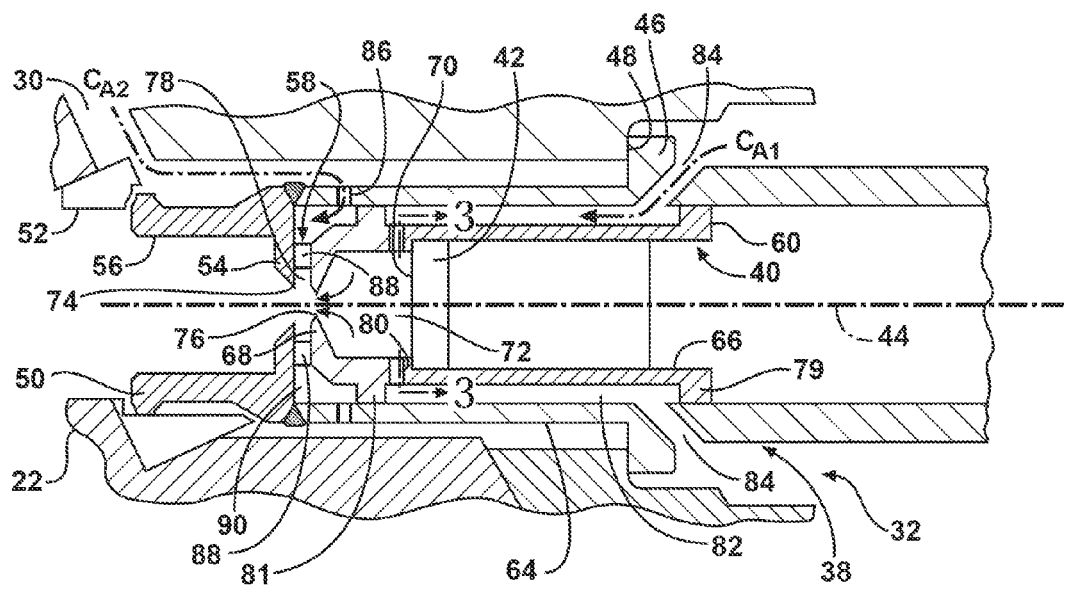
FIG. 2 is a cross-sectional view through an inner end portion of a viewing tube assembly for the monitoring system.

Referring to FIG. 2, the illustrated viewing tube assembly 32 comprises a tubular lens tube 38 and a lens housing 40 located within the lens tube 38. The lens housing 40 supports an optical element 42 which may comprise one or more lenses aligned along a longitudinal axis 44 of the viewing tube assembly 32 for transmitting an optical image from the inner end 34 to the outer end 36 of the viewing tube assembly 32. It should be understood that although a specific optical element is illustrated for the purposes of discussion of the invention, such illustration is provided for exemplary purposes and other, or additional, optical elements 42 may be included in the viewing tube assembly 32 including, for example, an optical element 42 comprising optical fibers or other optical transmission means.

As shown in FIG. 2, the lens tube 38 includes structure for engaging the inner casing wall 20. For example, the lens tube 38 may include a flange 46 engaging a cooperating surface 48 of the inner casing wall 20 to define an axial position for the lens tube 38, and further includes an end portion 50 that may be provided for engagement with a bushing 52 positioned between the end portion 50 and the shroud structure 22. The end portion 50 of the lens tube 38 defines a generally cylindrical open area for permitting passage of light from one or more components, i.e., blades 14, to the optical element 42 within the viewing tube assembly 32. Further, the end portion 50 may include a flange 54 extending radially inwardly from an inner end surface 56 of the lens tube 38 and forming a support structure for engagement by an end portion 58 of the lens housing 40.

Figure 4:
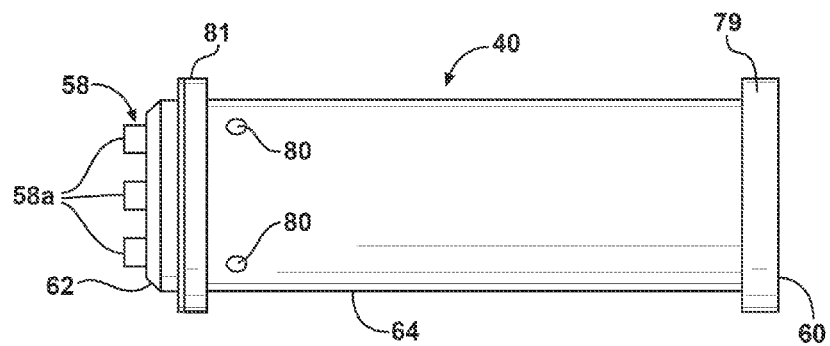
FIG. 4 is a side view of a lens housing for the viewing tube assembly.

Referring to FIGS. 2 and 4, the lens housing 40 comprises a tubular member having a first end 60 and a second end 62, and includes an exterior surface 64 and an interior surface 66 defining an interior portion of the viewing tube assembly 32. The optical element 42 may be supported on the interior surface 66 at a location between the first and second ends 60, 62. An aperture wall 68 extends radially inwardly from the interior surface 66 and is axially spaced from an inner side 70 of the optical element 42 to define a cooling and purge chamber 72 between the aperture wall 68 and the optical element 42. The optical element 42 prevents passage of gases from the chamber 72 past the optical element 42 into the viewing tube assembly 32.

The flange 54 includes an opening 74 for permitting passage of light from the hot gas path 24 into the viewing tube assembly 32. Further, the aperture wall 68 includes a knife edge optical aperture 76 for permitting passage of light into the lens housing 40, and for defining a field of view for imaging a location on a component, i.e., the turbine blade 14, to the optical element 42. The optical aperture 76 is a substantially small opening relative to the diameter of the optical element 42, i.e., relative to a lens, where the diameter of the optical element 42 (lens) is at least 5 times greater than the diameter of the optical aperture 76. In addition, the end portion 58 of the lens housing 40 spaces the aperture wall 68 from the flange 54 a predetermined axial distance to define an annular area 78 therebetween surrounding the optical aperture 76.

Figure 3:
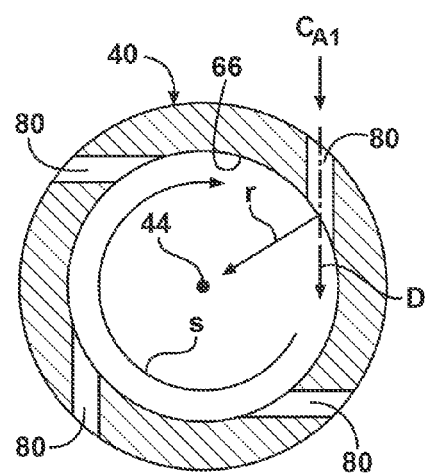
FIG. 3 is a cross-sectional view taken along line 3-3 in FIG. 2.

Referring to FIGS. 2 and 3, the lens housing 40 includes at least one swirl passage 80 for passage of cool air into the chamber 72, and preferably includes a plurality of circumferentially spaced swirl passages 80. The swirl passages 80 are positioned at an axial location along the chamber 72 that is substantially close to the optical element 42, and lie parallel to a plane generally perpendicular to the longitudinal axis 44, such as a plane defined by the inner side 70 of the optical element 42.

Figure 5:
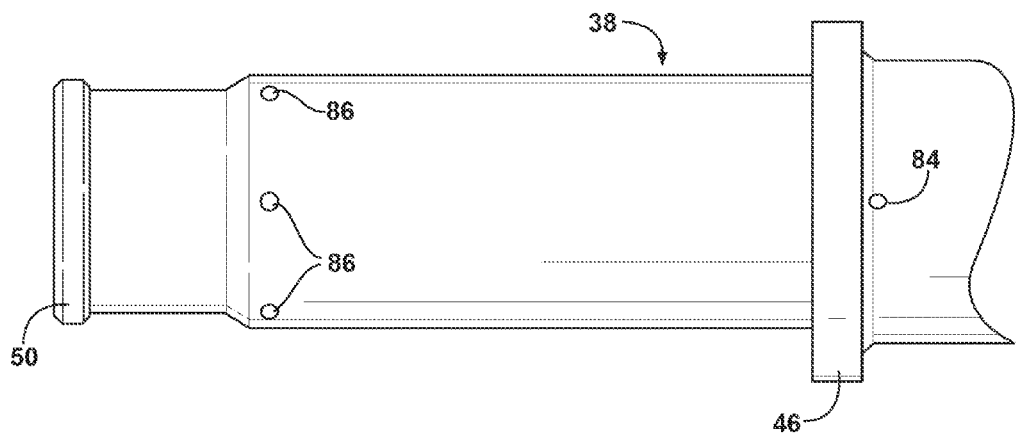
FIG. 5 is a side view of a portion of a lens tube for the viewing tube assembly.

As seen in FIG. 4, the lens housing 40 includes a first flange 79 adjacent to the first end 60 and a second flange 81 adjacent to the second end 62. The first and second flanges 79, 81 space the exterior surface 64 of the lens housing 40 from the interior of the lens tube 38, such that a cooling air supply passage 82 is defined in the gap between the lens tube 38 and the lens housing 40 for receiving cooling air $C_{A1}$ (FIG. 2). The cooling air $C_{A1}$ provided to the air passage 82 may comprise shell air passing into the viewing tube assembly 32 from the shell area 28. For example, the lens tube 38 may be provided with one or more holes 84 (see also FIG. 5) for passage of shell supplied cooling air $C_{A1}$ from a location outside of the lens tube 38 into the air passage 82. The total flow area provided into the chamber 72 by the swirl passages 80 is greater than the flow area provided out of the chamber 72 through the optical aperture 76, such that a pressure substantially as great as the pressure of the shell air is maintained within the chamber 72.

As seen in FIG. 3, the swirl passages 80 direct the cooling air $C_{A1}$ entering the chamber 72 to flow in an inward direction D that is transverse to a radial direction r from the interior surface 66 at the swirl passage 80 and passing through the longitudinal axis 44 of the viewing tube assembly 32, such that the passages 80 effect a swirling movement of the cooling air $C_{A1}$ entering the chamber 72. In particular, the swirl passages 80 are oriented to direct the cooling air $C_{A1}$ to enter the chamber 72 in a direction D generally tangential to the interior surface 66 of the lens housing 40, effecting swirling movement S of the cooling air $C_{A1}$ in a circumferential direction adjacent to the optical element 42.

It may be noted that hot gas flowing through the hot gas path 24 may tend to flow into the viewing tube assembly 32, and the cooling air $C_{A1}$ provided to the chamber 72 provides an increased pressure within the chamber 72 that prevents or limits entry of the hot gases while also providing convective cooling to the optical element 42. Further, it is believed that the swirling movement S of the cooling air $C_{A1}$ is operable to decrease deposition of contaminants on the optical element 42, such as by effecting a sweeping or purging of contaminants from the inner side 70 of the optical element 42. The swirling movement of the cooling air $C_{A1}$ further operates to increase convective cooling by increased movement of the cooling air at the surface of the optical element 42.

Referring to FIG. 2, additional or secondary cooling air $C_{A2}$ may be provided to the viewing tube assembly 32 through openings 86 (FIG. 5) formed in the lens tube 38 for passage of the secondary cooling air $C_{A2}$ to the annular area 78. In particular, the secondary cooling air $C_{A2}$ passes through the openings 86 adjacent to the end portion 58 of the lens housing 40, and the secondary cooling air $C_{A2}$ enters a gap area 90 between the lens tube 38 and the lens housing 40 on a side of the second flange 81 opposite from the air passage 82 for the shell supplied cooling air $C_{A1}$. The end portion 58 of the lens housing 40 may comprise a plurality of circumferentially spaced posts 58a (FIG. 4) defining air passages 88 between adjacent posts 58a into the annular area 78. The secondary cooling air $C_{A2}$ may comprise vane cooling air supplied from the vane cooling passage 30, and typically comprises air at a lower pressure than the cooling air $C_{A1}$ supplied from the shell area 28. The secondary cooling air $C_{A2}$ may be provided to further increase the cooling air pressure within the viewing tube assembly 32.

The combined pressure of the shell supplied cooling air $C_{A1}$ and the secondary cooling air $C_{A2}$ is greater than the pressure of the hot gas flowing in the hot gas path 24. Hence, the pressure provided by the cooling air flows $C_{A1}$, $C_{A2}$ is operable resist inflow of hot gas into the viewing tube assembly 32.

The present invention facilitates use of optical monitoring systems during operation of a gas turbine engine where the operating temperature of the optical element 42, i.e., one or more lenses, is typically lower than the temperature of the gases passing through the hot gas path 24. Hence, the present system may facilitate long term operation of the optical system 10 by providing enhanced cooling and protection from contamination for the optical element 42 of the optical system 10.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A monitoring system for a gas turbine engine, the monitoring system comprising:
   a viewing tube assembly having an exterior surface and an interior surface, and an inner end and an outer end, the inner end located adjacent to a hot gas flow path within the gas turbine engine and the outer end located adjacent to an outer casing of the gas turbine engine;
   wherein the viewing tube assembly comprises a lens tube and a lens housing located within the lens tube at the inner end of the viewing tube assembly;
   an aperture wall located at the inner end of the viewing tube assembly, the aperture wall extending radially inwardly relative to the interior surface of the viewing tube assembly at the inner end thereof;
   an optical element located within the viewing tube assembly adjacent to the inner end and spaced from the aperture wall to define a cooling and purge chamber therebetween;
   an aperture defined in the aperture wall for passage of light from the hot gas flow path to the optical element, the aperture having a diameter smaller than a diameter of the optical element;
   a flange extending radially inwardly from an inner surface of the lens tube at the inner end, the flange including a opening for passage of light from the hot gas flow path, the opening having a diameter smaller than the diameter of the optical element;
   the flange being spaced axially from the aperture wall on a side of the aperture wall opposite from the chamber to defined an annular area therebetween, the annular area surrounding the aperture and extending radially outwardly from the opening in the flange;
   one or more swirl passages defined in the lens housing between the aperture wall and the optical element for passage of cooling air from a location outside the viewing tube assembly into the chamber and supplied from a first source of cooling air, wherein the one or more swirl passages effect a swirling movement of air in a circumferential direction within the chamber; and
   one or more openings defined through the lens tube between the aperture wall and the flange for passage of air from a second source of cooling air into the annular area between the aperture wall and the flange.

2. The monitoring system as in claim 1, wherein the one or more swirl passages direct the cooling air entering the chamber to flow in an inward direction transverse to a radial direction passing through a central longitudinal axis of the viewing tube assembly.

3. The monitoring system as in claim 2, wherein the one or more swirl passages are oriented to direct the cooling air to enter the chamber generally tangential to an interior surface of the interior portion of the viewing tube assembly.

4. The monitoring system as in claim 2, wherein the one or more swirl passages lie parallel to a plane generally perpendicular to the longitudinal axis.

5. The monitoring system as in claim 1, wherein an axially extending air passage is defined in a gap between the lens tube and the lens housing for supplying cooling air to the one or more swirl passages.

6. The monitoring system as in claim 5, wherein cooling air is provided to the axially extending air passage from shell air passing between a radially outer casing wall and a radially inner casing wall of the gas turbine engine.

7. The monitoring system as in claim 6, including a vane cooling air passage defined between the inner casing wall and an annular shroud structure of the gas turbine engine, wherein the one or more openings defined through the lens tube provide for passage of vane cooling air from the vane cooling air passage outside the viewing tube assembly into the annular area.

8. The monitoring system as in claim 7, wherein a pressure of the shell air provided to the chamber is greater than a pressure of the vane air provided to the annular area.

9. The monitoring system as in claim 1, wherein the optical element comprises a lens, and a diameter of the lens is at least approximately 5 times greater than a diameter of the aperture.

10. A monitoring system for a gas turbine engine comprising a radially outer casing wall and a radially inner casing surrounding a hot gas path through the turbine engine, the monitoring system comprising:
    a viewing tube assembly having an exterior surface and an interior surface, and an inner end and an outer end, the inner end located adjacent to the inner casing wall and the outer end located adjacent to the outer casing wall of the gas turbine engine;
    wherein the viewing tube assembly comprises a lens tube and a lens housing located within the lens tube at the inner end of the viewing tube assembly;
    an aperture wall located at the inner end of the viewing tube assembly, the aperture wall extending radially inwardly relative to the interior surface of the viewing tube assembly at the inner end thereof;
    an optical element located within the viewing tube assembly adjacent to the inner end and spaced from the aperture wall to define a cooling and purge chamber therebetween;

an aperture defined in the aperture wall for passage of light from the hot gas flow path to the optical element;

a flange extending radially inwardly from an inner surface of the lens tube at the inner end, the flange including an opening for passage of light from the hot gas flow path, the opening having a diameter smaller than the diameter of the optical element;

the flange being spaced axially from the aperture wall on a side of the aperture wall opposite from the chamber to define an annular area therebetween, the annular area surrounding the aperture and extending radially outwardly from the opening in the flange;

a plurality of circumferentially spaced swirl passages extending from an exterior surface to the interior surface of the lens housing and located adjacent to the optical element for passage of cooling air from a location outside the viewing tube assembly into the chamber and supplied from a first source of cooling air, wherein the swirl passages are each angled relative to an inward direction passing through a central longitudinal axis of the viewing tube assembly to effect a swirling movement of air in a circumferential direction within the chamber and subsequent flow of the cooling air out of the chamber through the aperture; and one or more openings defined through the lens tube between the aperture wall and the flange for passage of air from a second source of cooling air into the annular area between the aperture wall and the flange.

11. The monitoring system as in claim 10, wherein the swirl passages lie parallel to a plane generally perpendicular to the longitudinal axis.

12. The monitoring system as in claim 11, wherein the swirl passages are oriented to direct the cooling air to enter the chamber generally tangential to the interior surface of the viewing tube assembly.

13. The monitoring system as in claim 10, wherein an axially extending air passage is defined in a gap between the lens tube and the lens housing for supplying cooling air to the swirl passages.

14. The monitoring system as in claim 13, wherein cooling air is provided to the axially extending air passage from shell air passing between the outer casing wall and the inner casing wall, and including a vane cooling air passage defined between the inner casing wall and an annular shroud structure of the gas turbine engine, wherein the one or more openings defined through the lens tube provide for passage of vane cooling air from the vane cooling air passage outside the viewing tube assembly into the annular area.

15. The monitoring system as in claim 14, wherein a pressure of the shell air provided to the chamber is greater than a pressure of the vane cooling air provided to the annular area.

16. The monitoring system as in claim 10, wherein the total flow area of the swirl passages is greater than a flow area of the aperture.

17. The monitoring system as in claim 10, wherein the optical element comprises a lens, and a diameter of the lens is at least approximately 5 times greater than a diameter of the aperture.

* * * * *